United States Patent
Mishra et al.

(10) Patent No.: US 9,795,311 B2
(45) Date of Patent: Oct. 24, 2017

(54) METHOD FOR INTRALUMINAL PRESSURE DETECTION FOR DIVERTICULAR DISEASE

(71) Applicant: Empire Technology Development LLC, Wilmington, DE (US)

(72) Inventors: Himanshu Mishra, Uttar Pradesh (IN); Mona Sharma, Madhya Pradesh (IN); Mandar Shirish Dixit, Uttar Pradesh (IN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 15/355,616

(22) Filed: Nov. 18, 2016

(65) Prior Publication Data
US 2017/0065192 A1  Mar. 9, 2017

Related U.S. Application Data

(62) Division of application No. 14/830,547, filed on Aug. 19, 2015, now Pat. No. 9,534,977.

(30) Foreign Application Priority Data
Aug. 20, 2014 (IN) .......................... 2359/DEL/2014

(51) Int. Cl.
*A61K 9/48* (2006.01)
*A61B 5/03* (2006.01)
(Continued)

(52) U.S. Cl.
CPC .............. *A61B 5/03* (2013.01); *A61B 5/4255* (2013.01); *A61K 9/0053* (2013.01); *A61K 9/2072* (2013.01); *A61K 9/4816* (2013.01); *A61K 9/4825* (2013.01); *A61K 9/4833* (2013.01); *A61K 9/4866* (2013.01); *A61K 9/4891* (2013.01); *A61K 47/32* (2013.01); *A61K 47/38* (2013.01); *G01L 1/00* (2013.01);
(Continued)

(58) Field of Classification Search
CPC .......................... A61K 9/4891; A61K 9/4866
See application file for complete search history.

(56) References Cited

U.S. PATENT DOCUMENTS 7,144,366 B2   12/2006   Takizawa et al.

OTHER PUBLICATIONS

Somchai Amornyotin, Capsule Endoscopy: A Ne Era of Gastrointestinal Endoscopy, "Edoscopy of the GI Tract", Mar. 2013.*
(Continued)

*Primary Examiner* — Carlos Azpuru
(74) *Attorney, Agent, or Firm* — Maschoff Brennan

(57) ABSTRACT

A pressure detection tablet is disclosed. The tablet is a capsule including a dye encapsulated within an inner coating, in which the inner coating is configured to rupture at a pressure equal to or greater than a pressure threshold. The tablet further includes an outer coating surrounding the capsule, in which the outer coating is configured to provide delivery of the capsule to a targeted site. The dye may be a non-metabolized, water soluble dye, such that a ruptured capsule releases the dye which can be visually detected in the urine. In some embodiments, the disclosure provides a method of making the tablet, using the tablet to detect peak pressure in the colon and reducing the risk of developing a colonic disorder.

20 Claims, 6 Drawing Sheets

(51) Int. Cl.
  G01L 1/00      (2006.01)
  G01N 33/493    (2006.01)
  G01M 3/02      (2006.01)
  A61K 47/32     (2006.01)
  A61K 47/38     (2006.01)
  A61B 5/00      (2006.01)
  A61K 9/00      (2006.01)
  A61K 9/20      (2006.01)

(52) U.S. Cl.
  CPC ............ *G01M 3/02* (2013.01); *G01N 33/493* (2013.01); *A61B 2562/0247* (2013.01); *A61B 2562/162* (2013.01)

(56) References Cited

OTHER PUBLICATIONS

"EUDRAGIS 100," Evonik Industries, accessed athttp://web.archive.org/web/20130812170408/http://eudragit.evonik.com/product/eudragit/en/products-services/eudragit-productsfenteric-formulations/s-100/Pages/default.aspx, Aug. 12, 2013, pp. 4.

"EUDRAGIT L 100-55," Evonik Industries, accessed athttp://web.archive.org/web/20130812171430/http://eudragit.evonik.com/product/eudragit/en/products-services/eudragit-products/enteric-formulations/I-100-55/Pages/default.aspx, Aug. 12, 2013, pp. 4.

"Chromoendoscopy," Technology Status Evaluation Report, Gastrointestinal Endoscopy, ASGE, vol. 66, No. 1, pp. 639-649 (2007).

Abdou, M. S., et al., "Study of peroral colonic and peritoneal absorption in normal and pathological conditions using a dye," Gut, vol. 7, No. 3, pp. 282-284 (Jun. 1966).

Bassotti, G., et al., "Contractile activity of the human colon: lessons from 24 hour studies," Gut., vol. 34, No. 1, pp. 129-133 (Jan. 1993).

Clemens, C.H.M., et al., "Tone and phasic motility of the left colon in diverticular disease," In Colonic sensory and motor function in irritable bowel syndrome and diverticular disease, Chapter 5, pp. 91-106 (2003).

Ghoshal, U.C.,"Capsule Endoscopy: A New Era of Gastrointestinal Endoscopy," in Endoscopy of GI Tract, Chapter 5, eds., Amomyotin, S., pp. 75-88 (Mar. 13, 2013).

Herold, A., et al., "Coloproctology," European Manual of Medicine, Springer books (2008).

Hobson, K.G., and Roberts, P.L., "Etiology and Pathophysiology of Diverticular Disease," Clinics in Colon and Rectal Surgery, vol. 17, No. 3, pp. 147-153 (Aug. 2004).

Leroi, A. M., et al., "Prolonged stationary colonic motility recording in seven patients with severe constipation secondary to antidepressants," Neurogastroenterology and Motility, vol. 12, No. 2, pp. 149-154 (Apr. 2000).

Narducci, F., et al., "Twenty four hour manometric recording of colonic motor activity in healthy man," Gut., vol. 28, No. 1, pp. 17-25 (Jan. 1987).

Painter, N. S., "Diverticular disease of colon," British Medical Journal, vol. 3, pp. 475-479 (Aug. 24, 1968).

Rajesh, A., et al., "Oral Colon Targeted Drug Delivery system: A review of current and novel perspectives," Journal of pharmaceutical and scientific innovation, vol. 1, No. 5, pp. 6-12 (Sep.-Oct. 2012).

* cited by examiner

METHOD FOR INTRALUMINAL PRESSURE DETECTION FOR DIVERTICULAR DISEASE

CROSS-REFERENCE TO RELATED APPLICATIONS

This application is a divisional under 35 U.S.C. §121 of and claims priority under 35 U.S.C. §120 to U.S. patent application Ser. No. 14/830,547, filed on Aug. 19, 2015, now U.S. Pat. No. 9,534,977, which claims the benefit of the foreign patent application IN 2359/DEL/2014, filed on Aug. 20, 2014, each of which are hereby incorporated by reference in their respective entireties.

BACKGROUND

Elevated intraluminal pressure is generated by phasic waves that propagate inside the colon. In healthy individuals, the intraluminal pressure does not generally exceed 200 mm Hg. However, physiological, neurological and age-related changes in the colon, such as elastin deposition, wall thickening, altered tone of colonic muscles, etc., may result in abnormal increases in the intraluminal pressure. Such abnormal increases may lead to formation of diverticular pouches, complications in existing diverticular pouches (e.g., mucosal damage, perforation, etc.), and/or recurrence of diverticular pouches at previously treated sites. Since colonic function is largely under the control of the enteric nervous system, it may not provide any perceivable sensory feedback of increased intraluminal pressure. Consequently, development of diverticular disease often remains unnoticed and asymptomatic for long periods of time.

SUMMARY

A pressure detection tablet is disclosed. The tablet includes: a capsule having a dye encapsulated within an inner coating, where the inner coating is configured to rupture at a pressure equal to or greater than a pressure threshold; and an outer coating surrounding the capsule, where the outer coating is configured to provide delivery of the capsule to a targeted site. The targeted site may be the colon. The dye is water-soluble and non-metabolizable. The inner coating is a pressure-sensitive polymer, the pressure threshold of which is selectable based on variations in at least one of a thickness, density, elasticity or a combination thereof of the inner coating. The outer coating includes a pH sensitive polymer that is insoluble at the acidic pH of the stomach and proximal small intestine but formulated to dissolve at a neutral pH or by bacterial degradation. The tablet can include at least two capsules surrounded by the outer coating such that the at least two capsules include different dyes and are configured to rupture at equal to or higher than a different pressure thresholds from one another.

A method for estimating peak pressure within the colon of a subject is disclosed. The method includes orally administering to the subject a pressure detection tablet, including a capsule including an inner coating configured to rupture when the pressure within the colon reaches or exceeds a pressure threshold; and a water-soluble, non-metabolizable dye encapsulated within the inner coating, in which the dye is absorbed by the colon and excreted by the kidneys upon rupture of the coating; and an outer coating surrounding the capsule, and configured to remain intact in the stomach and small intestine, thereby providing colon specific delivery of the capsule; observing the color of the subject's urine after a test period; and estimating the peak pressure in the colon during the test period, in which a normal urine color indicates that the peak pressure in the colon was below the threshold during the test period, and in which a urine color attributable to the dye indicates that the peak pressure in the colon reached or exceeded the threshold during the test period.

A method for reducing a risk of developing a colonic disorder due to a peak pressure with the colon in a subject is also disclosed. The method includes estimating peak pressure within the colon of the subject by orally administering to the subject a pressure detection tablet including a capsule including an inner coating configured to rupture when the pressure within the colon reaches or exceeds a pressure threshold; and a water-soluble, non-metabolizable dye encapsulated within the inner coating, in which the dye is absorbed by the colon and excreted by the kidneys upon rupture of the coating; and an outer coating surrounding the capsule, and configured to remain intact in the stomach and small intestine, thereby providing colon specific delivery of the capsule; observing the color of the subject's urine after a test period; and estimating the peak pressure in the colon during the test period, in which a normal urine color indicates that the peak pressure in the colon was below the threshold during the test period, and in which a urine color attributable to the dye indicates that the peak pressure in the colon reached or exceeded the threshold during the test period; administering a treatment to the subject if the observed urine color is attributable to the dye, in which the treatment is selected to reduce the peak pressure within the colon to below the threshold, thereby reducing the risk of colonic disorder.

In some embodiments, the pressure detection tablet includes at least two capsules surrounded by the inner coating and in which the at least two capsules include different dyes and are configured to rupture at a different pressure threshold from one another. The method of reducing risk can be repeated daily, biweekly, weekly, bimonthly, monthly, yearly, or as required. The step of administering a treatment can include administering a medication, an altered diet, a physical exercise regimen, or a combination thereof.

A method of making a pressure detection tablet is disclosed. The method includes encapsulating a water-soluble and non-metabolizable dye within an inner coating to obtain a capsule, in which the inner coating is configured to rupture at a pressure equal to or greater than a pressure threshold, and encapsulating the capsule within an outer coating, in which the outer coating is configured to provide delivery of the capsule to a targeted site. The inner coating includes a pressure-sensitive ethyl cellulose polymer and the pressure threshold for rupture of the inner coating is selectable based on variations in at least one of a thickness, density and elasticity of the inner coating. The pressure threshold can range from about 200 mm Hg to about 700 mm Hg. The outer coating includes a pH sensitive polymer that is formulated to be insoluble at the acidic pH of the stomach and proximal small intestine but formulated to dissolve at a neutral pH, or formulated to dissolve by bacterial degradation, or formulated to be a combination thereof.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1A:
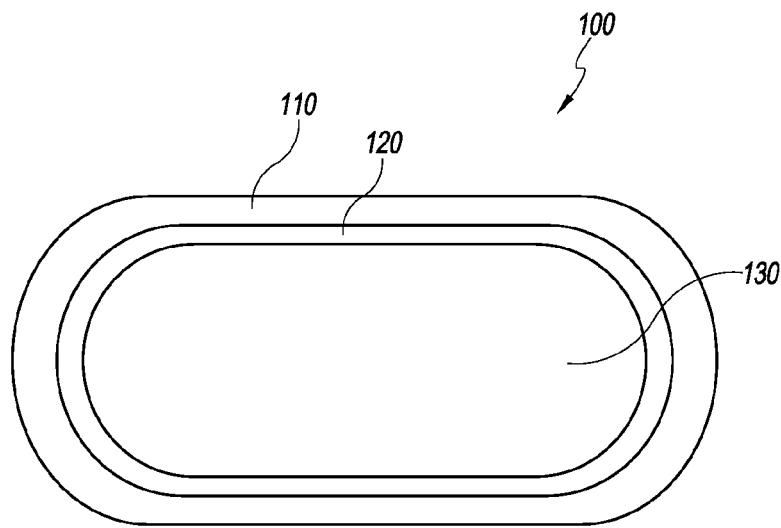
FIG. 1A is a cross-sectional view of a pressure detection tablet in accordance with an embodiment of the disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

A pressure detection tablet is disclosed. The tablet includes: a capsule having a dye encapsulated within an inner coating, where the inner coating is configured to rupture at a pressure equal to or greater than a pressure threshold; and an outer coating surrounding the capsule, where the outer coating is configured to provide delivery of the capsule to a targeted site. The targeted site may be the colon.

In some embodiments, the dye is water-soluble and non-metabolizable. Although not limiting, the dye may be selected from phenol red, methylene blue, eosin, pelargonin, aurantinidine, indigo carmine, cyanidin, myrtillin, tulipanin, violdelphin, betadine, sorbitol, and betalain.

In some embodiments, the inner coating includes a pressure-sensitive polymer. The pressure-sensitive polymer may not be soluble in water. The pressure-sensitive polymer may be ethyl cellulose, cellulose acetate butyrate, cellulose acetate phthalate or any similar cellulose acetate esters membranes.

The pressure threshold of the inner coating may be selectable based on variations in at least one of a thickness, density and elasticity of the inner coating. In some embodiments, the pressure threshold of the inner coating is selected to be equal to or greater than about 200 mm Hg. In other embodiments, the pressure threshold of the inner coating is selected to be equal to or less than about 700 mm Hg. In certain embodiments, the pressure threshold of the inner coating may be selected to be about 200, 210, 220, 230, 240, 250, 260, 270, 280, 290, 300, 310, 320, 330, 340, 350, 360, 370, 380, 390, or 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 mm Hg (or torr). In some embodiments, the targeted site is a colon.

The outer coating of the tablet may include a pH sensitive polymer that is insoluble at the acidic pH of the stomach and proximal small intestine. In certain embodiments, the pH sensitive polymer is a methacrylic acid ester, shellac or HPMC acetate succinate. In other embodiments, the pH sensitive polymer includes a copolymer of EUDRAGIT L (polymerized monomers of methacrylic acid and ethyl acrylate, wherein the ratio of free carboxylic acid to ester is 1:1) and EUDRAGIT S (polymerized monomers of methacrylic acid and methyl methacrylate, wherein the ratio of free carboxylic acid to ester is 1:2) polymers, formulated to dissolve at neutral pH. In some embodiments, the pH sensitive polymer includes a copolymer of EUDRAGIT L-100-55 (methacrylic acid and ethyl acrylate (1:1)) and EUDRAGIT S 100 (methacrylic acid and methyl methacrylate (1:2)), formulated to dissolve at neutral pH.

In some embodiments of the disclosed pressure detection tablet, the outer coating may also include azo polymers of styrene and 2-hydroxy methyl acrylate to facilitate dissolution of the outer layer in the colon through bacterial degradation.

In some embodiments, the disclosed pressure detection tablet can include at least two capsules within the inner coating and further surrounded by the outer coating. Some of the at least two capsules may include different dyes and different pressure thresholds from one another.

A method for estimating peak pressure within the colon of a subject is disclosed. The method includes orally administering to the subject a pressure detection tablet, including a capsule including an inner coating configured to rupture when the pressure within the colon reaches or exceeds a pressure threshold; and a water-soluble, non-metabolizable dye encapsulated within the inner coating, in which the dye is absorbed by the colon and excreted by the kidneys upon rupture of the coating; and an outer coating surrounding the capsule, and configured to remain intact in the stomach and small intestine, thereby providing colon specific delivery of the capsule; observing the color of the subject's urine after a test period; and estimating the peak pressure in the colon during the test period, in which a normal urine color indicates that the peak pressure in the colon was below the threshold during the test period, and in which a urine color attributable to the dye indicates that the peak pressure in the colon reached or exceeded the threshold during the test period.

In some embodiments, orally administering the pressure detection tablet includes at least first and second different capsules surrounded by the same outer coating, in which a thickness of the inner coating of the first capsule is less than a thickness of the inner coating of the second capsule, such that the first and second capsules are configured to rupture at first and second different pressure thresholds, the first pressure threshold being less than the second pressure threshold, and in which the first capsule has a first dye indicative of the first, lower, pressure threshold and the second capsule has a second dye indicative of the second, higher, pressure threshold.

In some embodiments, at least first and second different pressure detection tablets are orally administered as separate tablets, in which the first pressure detection tablet has a first capsule with a first dye and a first pressure threshold, and in which the second pressure detection tablet has a second capsule with a second dye and a second pressure threshold, the first pressure threshold being less than the second pressure threshold.

In some embodiments, estimating the peak pressure in the colon during the test period is based on the observed urine color, in which: (a) a normal urine color indicates that the peak pressure in the colon was below the first and second pressure thresholds during the test period; (b) a urine color attributable to the first dye indicates that the peak pressure in the colon reached or exceeded the first pressure threshold, but remained below the second pressure threshold during the test period; (c) a urine color attributable to a combination of the first and second dyes indicates that the peak pressure in the colon reached or exceeded the second pressure threshold during the test period.

A method for reducing a risk of developing a colonic disorder in a subject is also disclosed. The method includes: estimating peak pressure within the colon of the subject including: orally administering to the subject a pressure detection tablet, including: a capsule including an inner coating configured to rupture when the pressure within the colon reaches or exceeds a pressure threshold; and a water-soluble, non-metabolizable dye encapsulated within the inner coating, in which the dye is absorbed by the colon and excreted by the kidneys upon rupture of the coating; and an outer coating surrounding the capsule, and configured to remain intact in the stomach and small intestine, thereby providing colon specific delivery of the capsule; observing the color of the subject's urine after a test period; and estimating the peak pressure in the colon during the test period, in which a normal urine color indicates that the peak pressure in the colon was below the threshold during the test period, and in which a urine color attributable to the dye indicates that the peak pressure in the colon reached or exceeded the threshold during the test period; administering a treatment to the subject if the observed urine color is attributable to the dye, in which the treatment is selected to reduce the peak pressure within the colon to below the threshold. In some embodiments, the method steps are repeated at regular intervals. In some embodiments, the regular intervals are weekly or biweekly. In some embodiments, the method steps are repeated after the treatment to ensure that the treatment was effective. In some embodiments, if the treatment was not effective, an alternative treatment is provided to reduce the peak pressure and the method steps are repeated to ensure that the alternative treatment was effective. The tablet can be self-administered by the subject. If required, the tablet can be administered by a health care professional to the subject in need thereof.

Overview

Intraluminal pressures in the colon are generated due to phasic waves propagating inside the colon. In healthy individuals, these pressure values do not exceed 200 mm Hg. However, physiological and neurological changes in the colon (like elastin deposition, wall thickening, and altered tone of colonic muscles) may result in abnormal increase of intraluminal pressures. Since colonic function is part of the enteric nervous system, it does not provide any perceivable sensory feedback of this increased intraluminal pressure. Hence in many cases diverticulosis remains unnoticed and asymptomatic for long periods of time. Building up of chronic abnormal intraluminal pressure may increase development of diverticula disease in at least three ways. First, it may lead to formation of diverticula pouches in a colon having no diverticula pouches. Second, it may lead to complications like mucosal damage and perforation in already formed diverticula pouches. Third, it may lead to recurrence of diverticula pouches in a colon that has undergone treatment for existing diverticula pouches. Thus a simple, self-administered indicator of excessive intraluminal pressure in the colon could lead to more timely intervention, and may thereby prevent and/or slow development of diverticular disease and potentially help retain the colon in a prolonged healthy state.

Disclosed herein is such a simple, self-administered intraluminal pressure detection indicator and method, in the form of an oral tablet. This pressure detection tablet functions by giving a color indication in urine if and when the intraluminal pressures in the colon reach or exceed one or more threshold values, including for example, potentially unsafe values (greater than 200 mm Hg) for a healthy or a diverticulosis affected colon. In some embodiments, the pressure detection table may include a non-metabolizable, water-soluble dye encapsulated in a pressure sensitive capsule. This dye is released in the colon, for example, the descending/sigmoid colon when the intraluminal pressure exceeds a selected threshold value. The released dye is then absorbed into the blood through the colonic wall and excreted through the urine, thereby imparting an observable color to the urine. This tablet and method may be used to detect excessive pressures in the entire colon, ranging from ascending, transverse, descending, and sigmoidal parts of the colon. With this tablet and method it is possible to easily detect undesirable colonic changes due to elevated intraluminal pressure before the resulting complications, e.g., diverticula formation, start developing. In some embodiments, the early detection of elevated intraluminal pressure can be coupled with the adoption of prophylactic measures, such as down-regulating or managing the pressures in the colon.

Physiologic Background

Colonic motility is a complex phenomenon governed by many factors. Bowel movements are controlled in order to maximize absorption of nutrients and minerals and at the same time the waste matter is moved forward for expelling out of body. As part of squeezing the fecal matter through colonic contractions, active water absorption happens in the colon from the ascending colon to the sigmoidal colon. These activities are highly coordinated and programmed in the body. Two types of contractions of colonic smooth muscles bring about colonic motility—phasic and tonic. Phasic contractions are generated in response to spike potential which lasts for a few seconds and causes an elevation of intraluminal pressure. Tonic contractions are less well defined, last longer and may not be associated with intraluminal pressure. The pattern of colonic contractions can be classified into four categories: single non-propagating, anterograde, retrograde, and periodic colonic motor activity. Anterograde pressure waves also known as High Amplitude Propagated Contractions (HAPCs) start from cecum and span the entire colonic length. They are responsible for colonic transport, occur a few times a day, and may be induced e.g., by awakening, meals, etc. The amplitude and area covered increases from the ascending colon to the sigmoidal colon, with sigmoidal colon showing average pressure values of 160 mm Hg (highest among all types of waves).

High intraluminal pressure (average value of greater than 200 mm Hg in diverticulosis affected patients) is responsible for both development and progression of disease. The diverticular disease initiates with formation of mucosal outpouching in the colon (predominantly in the sigmoidal colon) called diverticulum and transforms to complications like abscess, perforation and colonic infections as the disease progresses.

However, since nervous innervation of the colon is predominantly part of the enteric nervous system, it does not provide any perceivable sensory feedback of increased intraluminal pressure. Therefore, disease progress may be asymptomatic for long periods of time, thus being diagnosed only when the disease has progressed to a symptomatic stage. This delay in disease diagnosis itself predisposes patients to irreversible progression of the disease causing irreversible physiological damage to the colon. Additionally, diagnosis and investigative techniques available for diverticular disease are only applicable once symptoms are evident to a patient, thus preventing early detection. As a result, at least some asymptomatic patients may become symptomatic if the contributing factors of disease are not controlled. Since we know that increased intraluminal pressure is a contributor to diverticular disease development, its early detection may help predict predisposition of individuals for diverticulosis and therefore prevention of the disease. Moreover, for uncomplicated diverticulosis, disease progression may be delayed if abnormal intraluminal pressures are avoided or therapeutically mitigated.

Pressure Detection Tablet

Figure 1B:
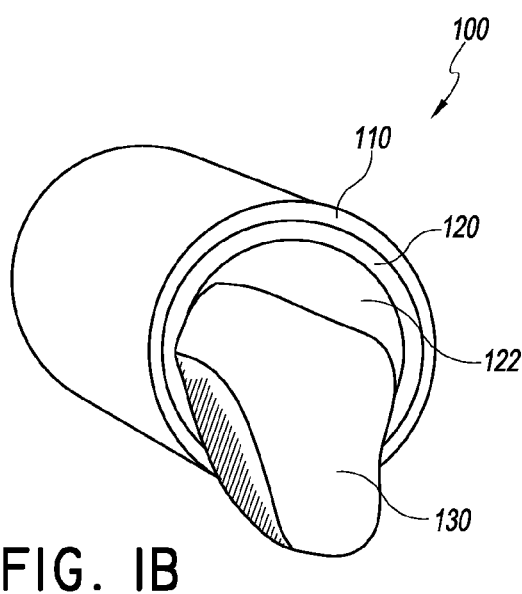
FIG. 1B is a cross-sectional perspective view of the pressure detection tablet illustrated in FIG. 1.

With reference to FIG. 1A a cross-sectional view of a pressure detection tablet 100 is shown in accordance with one embodiment. The illustrated tablet 100 has an outer coating 110, and inner coating 120, and a dye 130, which is enclosed within the inner coating 120. FIG. 1B is a cross-sectional perspective view of the same tablet shown in FIG. 1A, illustrating the dye 130, in liquid form, partially pouring out of the tablet. The outer coating 110 of the tablet 100 substantially prevents the tablet from opening in the stomach and small intestine. The outer coating 110 may also provide preferential targeting to a specific part of the colon. This preferential targeting may be pH-based and/or based on susceptibility to degradation by bacteria in the colon. Another function of the outer coating 110 may be to absorb shock and prevent external pressure transfer to the underlying inner coating 120. The inner coating 120 encapsulates the indicator dye 130. The inner coating 120 may be made from a pressure sensitive material, such as a polymer, the properties of which can be custom designed to provide a dye-impermeable membrane having a selected rupture pressure. The thickness, density and elasticity of this inner coating can be modulated to rupture at or above a selected threshold intraluminal pressure. Typically, intraluminal pressure attains a maximum value in the descending and/or sigmoidal colon. This maximum in healthy individuals is less than or equal to about 200 mm Hg during high amplitude pressure waves.

Figure 2:
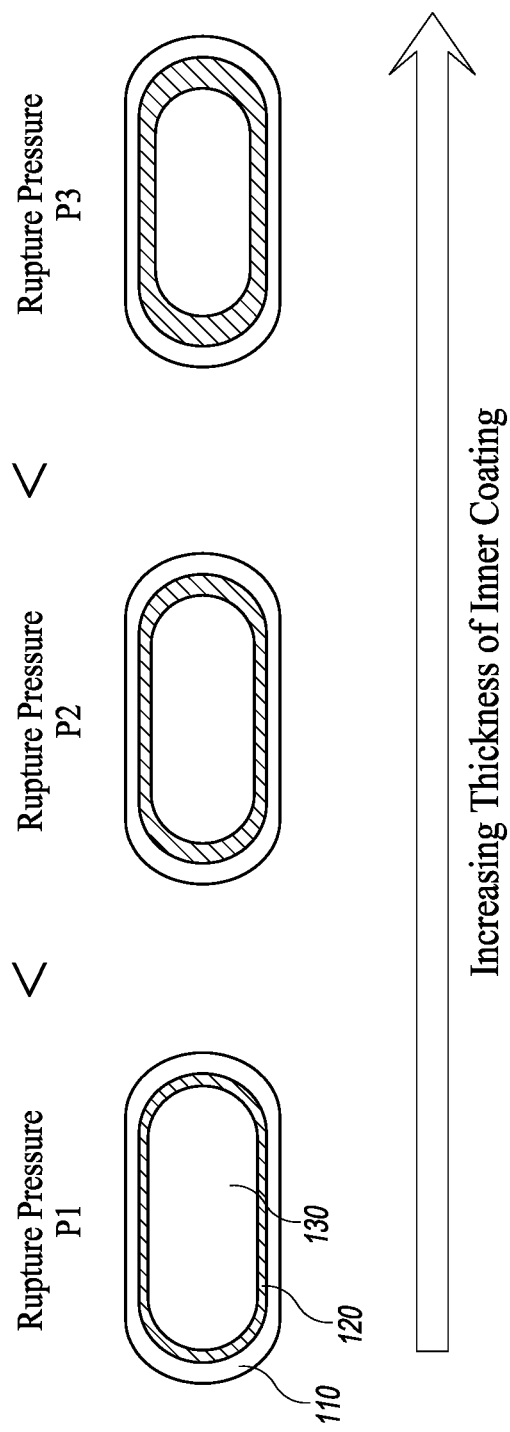
FIG. 2 shows the relationship between rupture pressure threshold and the cross-sectional structure of a pressure detection tablet.

With reference to FIG. 2, the relationship between inner coating thickness and rupture pressure is illustrated schematically. The inner coating 120 underlies the outer coating 110 and encapsulates the dye 130. The tablet on the left is designed to rupture at a pressure threshold of P1. Thus, the thickness of the inner coating 120 has a $P_{rupture}$ of P1. The tablet in the center is designed to rupture at a pressure threshold of P2, where P2 is greater than P1. Thus, the thickness of the inner coating of the center tablet has a $P_{rupture}$ of P2. The tablet on the right is designed to rupture at a pressure threshold of P3 where P3 is greater than P2. Thus, the thickness of the inner coating of the tablet on the right has a $P_{rupture}$ of P3.

Figure 3:
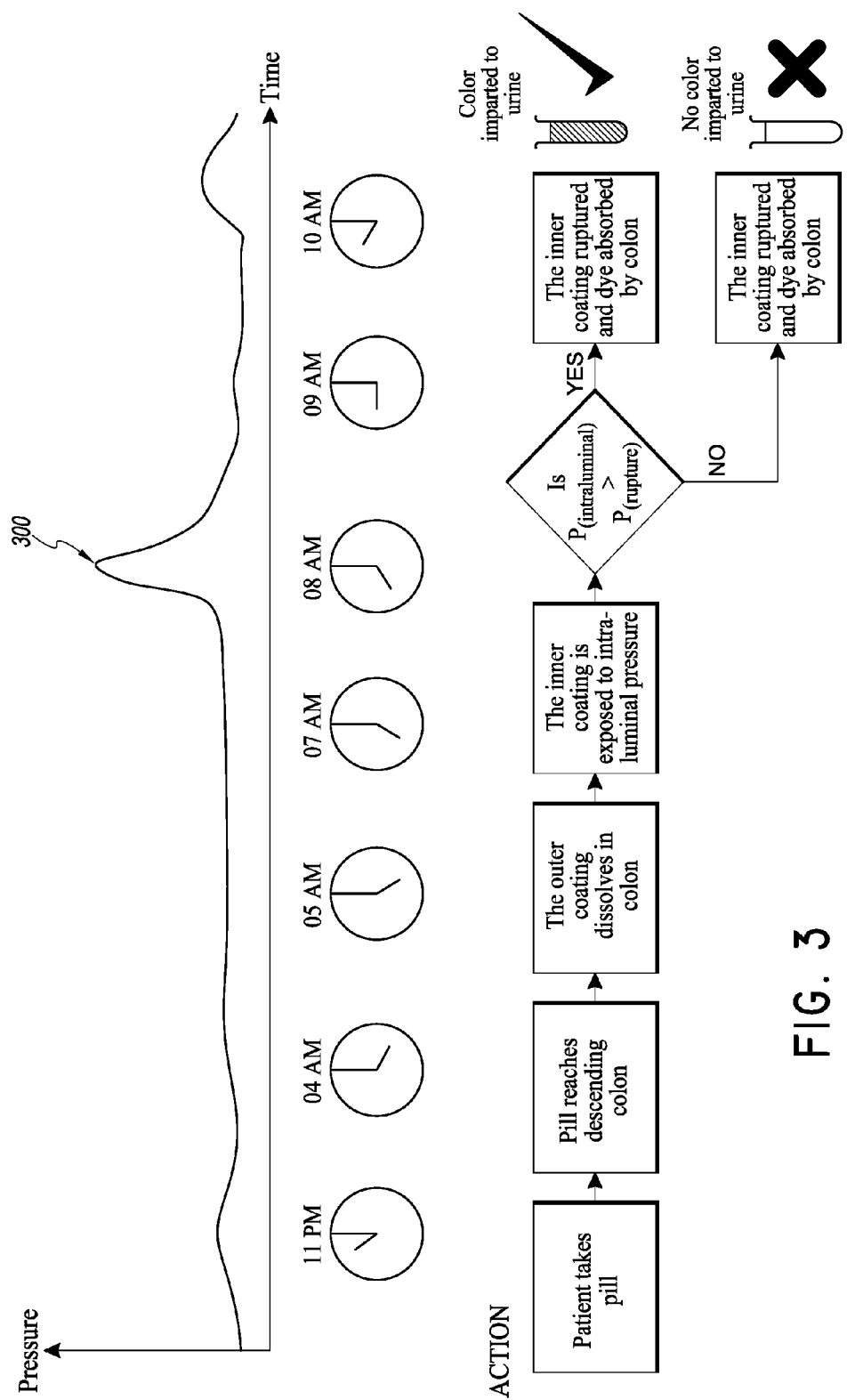
FIG. 3 is a schematic diagram of how one embodiment of the pressure detection tablet works.

With reference to FIG. 3, the functionality of one particular embodiment of the disclosure is depicted in a diagram. The peak on the graph 300 is the high amplitude pressure wave.

Figure 4B:
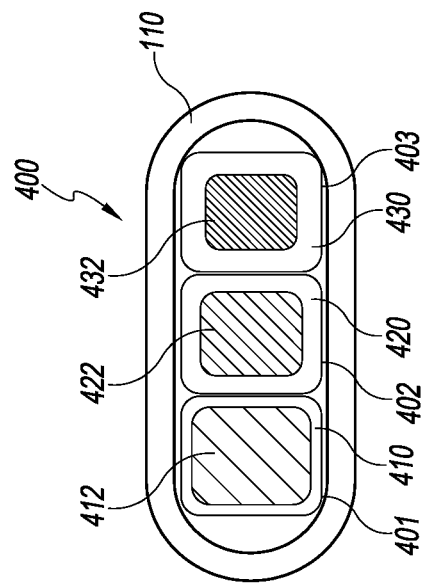
FIG. 4B is a cross-sectional view of a pressure detection table in accordance with another embodiment of the disclosure, including two or more capsules, in which each capsule has a different inner coating and a different dye therein.
Figure 4A:
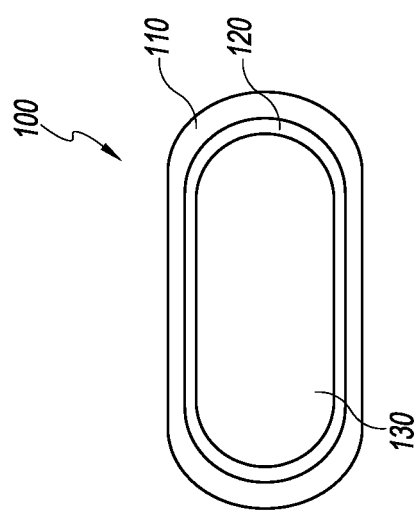
FIG. 4A is a cross-sectional view of a pressure detection tablet in accordance with another embodiment of the disclosure.

With reference to FIG. 4A, a cross-sectional view of a different embodiment of the pressure detection tablet 400 is shown. The illustrated tablet 400 has an outer coating 110 similar to the tablet illustrated and described above with reference to FIG. 1A. However, inside the outer coating, two or more capsules of macrospheres may be included, in which each macrosphere has a different inner coating and a different dye (FIG. 4B). In the illustrated embodiment (FIG. 4B), three macrospheres 401, 402, and 403 are shown, where the three inner coatings individually rupture at different pressures 410 (T1), 420 (T2), and 430 (T3). For instance, 410 may be a thickness that ruptures at 220 mm Hg, 420 may be a thickness that ruptures at 270 mm Hg, and 430 may be a thickness that ruptures at 320 mm Hg. Of course, the macrospheres may be designed to provide any rupture pressure range. Each inner coating encapsulates a dye 412, 422, and 432 each of a different of color. Any colored dyes may be used, although yellow and orange dyes and combinations are less desirable because visual detection of a change in urine color is more difficult with dye colors that are similar to the color of urine. Examples of desirable dye colors include blue, red, green, purple, brown, pink (see Table 2 below).

Figure 5:
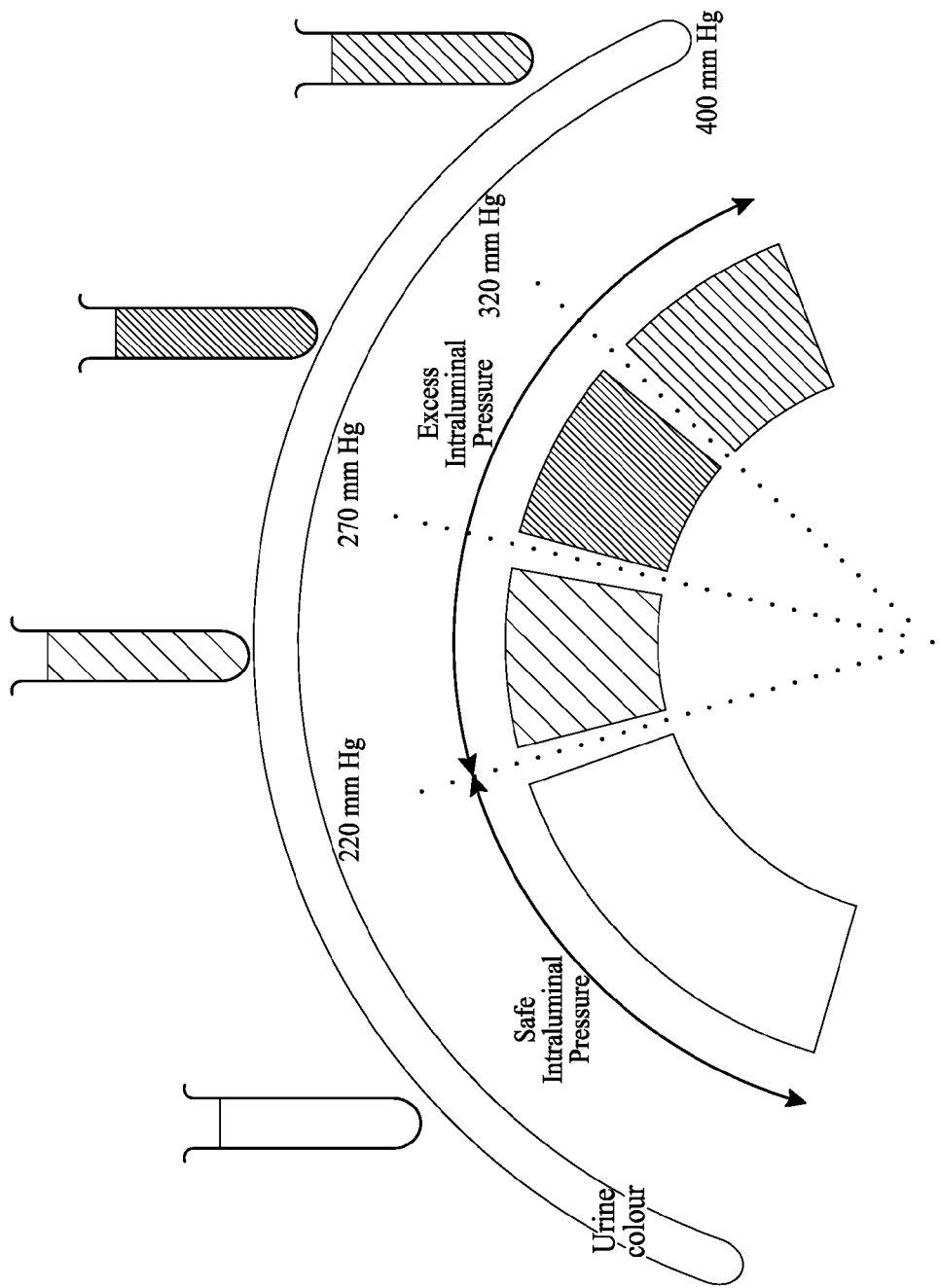
FIG. 5 is a diagram of how different urine colors may be indicative of different ranges of intraluminal pressures.

With reference to FIG. 5, the relationship between the color of the urine and the intraluminal pressure is illustrated schematically for an embodiment with three capsules of macrospheres whose inner coatings individually rupture at different pressures, 410 (T1), 420 (T2), and 430 (T3), with reference to FIG. 4. If the intraluminal pressure is between 220 mm Hg and 270 mm Hg, then the inner coating with T1 will rupture and the color of the urine will be of the dye encapsulated by the inner coating with T1. If the intraluminal pressure is between 270 mm Hg and 320 mm Hg, then the inner coatings with both T1 and T2 will rupture, and the color of the urine will be a mix of the dyes encapsulated by T1 and T2. If the intraluminal pressure is greater than 320 mm Hg, then the inner coatings with T1, T2 and T3 will all rupture, and the color of the urine will be a mix of the dyes encapsulated by T1, T2 and T3. Thus, the range of pressures being reached in a colon can be quantitatively estimated apart from just a qualitative assessment of excess pressures. The pressure values in FIG. 5 refer to peak pressures, and rupturing may occur as soon as the peak pressure is reached.

Figure 6:
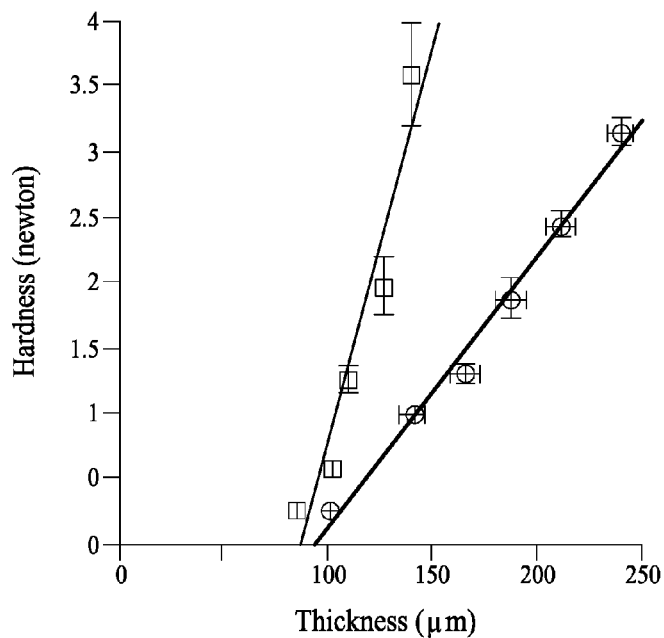
FIG. 6 is a graph depicting that the ethyl cellulose coating membrane hardness is linearly proportional to the ethyl cellulose coating membrane thickness.

With reference to FIG. 6, a graph is depicted showing that the ethyl cellulose coating membrane hardness is linearly proportional to the ethyl cellulose coating membrane thickness (hardness is measured as force in Newton, which is the pressure over unit area). The relationship between the thickness of ethyl cellulose and rupture pressure is assumed to be linear. FIG. 6 also shows that capsules of different sizes show different disintegration behavior as shown by the two different lines.

Figure 7:
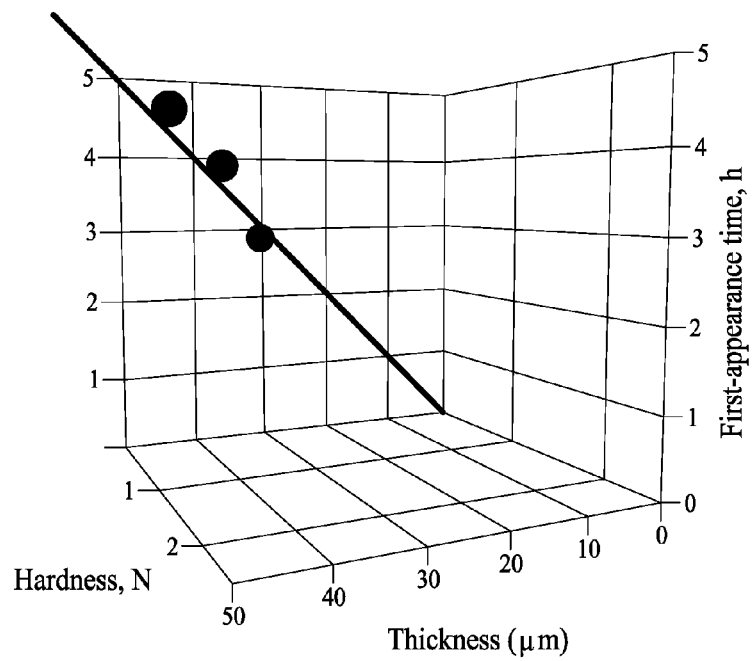
FIG. 7 is a graph depicting that the time of drug release from a pressure controlled drug capsule proportionally increases with the thickness of the ethyl cellulose membrane.

With reference to FIG. 7, a graph is depicted showing that the time of drug release from a pressure controlled drug capsule proportionally increases with the thickness of the ethyl cellulose membrane. Colonic luminal pressures increase from the ascending to sigmoidal colon, which causes high thickness capsules disintegrate at delayed time. Hence, it is possible to make capsules which disrupt at higher pressures and later in the colon by increasing the thickness of the ethyl cellulose coating membrane.

Outer Coating—The outer coating provides for colon specific delivery of the tablet. This coating prevents the tablet from opening in stomach and small intestine. The outer coating may also target delivery of the underlying pressure-sensitive capsule (with dye) to a specific part of colon. Another function of this coating is to absorb shocks and prevent external pressure transfer to the inner coating. TABLE 1 sets forth functional and material aspects of the outer coating, as well as the inner coating and dye in accordance with some embodiments of the disclosed pressure detection tablet.

TABLE 1

| Components of Tablet | Functional Properties | Exemplary (non-limiting) Materials | Variable Design Parameters |
|---|---|---|---|
| Outer Coating | shield the inner coating in stomach and small intestine enable targeted (pH-triggered) opening in descending colon | copolymer of Eudragit L100-55 and Eudragit S100 | pH-triggered dissolution can be modified by varying the proportions of Eudragit polymers |
| | absorb excess intraluminal pressure prevent internal rupturing | azo polymers of styrene and 2-hydroxy methyl acrylate | pressure tolerance and absorption can be modified by varying polymer cross-linking density |
| Inner Coating | rupture at selected pressure water insoluble resist enzymatic degradation | ethyl cellulose | rupture pressure can be selected/modified by varying polymer thickness and density |
| Dye | water soluble non-metabolizable biocompatible excreted distinct color resistant to degradation in colon | phenol red methylene blue | different rupture pressures can be color-coded dye may be gel or liquid to accommodate pressure build up inside capsule |

The outer coating may be made from any of a variety of polymers. In one embodiment, the outer coating includes a pH-sensitive polymer, in which for example, the polymer may degrade or dissolve at or above a selected pH. More particularly, the pH sensitive polymer of the outer coating may dissolve at a pH of about 7.0, 7.1, 7.2, 7.3, 7.4, 7.5, 7.6, 7.7, 7.8, 8.0, and above. The pH sensitive outer coating may remain intact at acidic pH conditions encountered in the stomach and small intestine, but degrade or dissolve at neutral to alkaline pH conditions encountered in the colon. In one particular embodiment, the pH sensitive polymer is a methacrylic acid ester. In another embodiment, the outer coating may include a copolymer of EUDRAGIT L100-55 and EUDRAGIT S 100. The proportions of each polymer in the copolymer can be varied to dissolve in a pH specific manner in a particular part of the colon. In another embodiment, the outer coating may include an azo copolymer of styrene and 2-hydroxy methyl acrylate. The cross-linking density of the azo polymer may be varied to accomplish targeted delivery to the colon. Use of an enteric outer coating to achieve colon-specific delivery has been described for colon-specific drug delivery.

In some embodiments, the desired functions of the outer coating are to: protect the contents of the inner capsule(s) from the acidic pH of stomach, and remain intact until the tablet has reached the target destination (e.g., the colon), upon which the outer coating should release the pressure-sensitive capsule(s) containing the indicator dye(s). Release of contents in the colon, i.e., dissolution of outer layer can be achieved by one or both of at least two different mechanisms: (1) pH change in the colon compromising the integrity of the outer coating, e.g., the Eudragit co-polymers; and (2) bacterial degradation of the outer coating in the colon, e.g., azo polymers of styrene and 2-hydroxy methyl acrylate. While either one or both strategies (e.g., polymers) may be used to provide colon-specific delivery, in some embodiments, pH-dependent dissolution of the outer coating (Eudragit copolymers) may be preferred.

Inner Coating—The inner coating which forms a capsule that encompasses an indicator dye is made of a pressure sensitive component (e.g., ethyl cellulose). The inner coating may be custom designed to rupture at a selected intraluminal pressure. In some embodiments, the inner coating forms an impermeable membrane. The thickness, density and elasticity of the inner coating can be modulated to rupture at or above a desired intraluminal pressure. Typically, intraluminal pressure attains a maximum value in the descending and sigmoidal colon and hence such value in healthy individuals can be benchmarked for constructing the basic pressure detection tablet. Based on current literature, a safe intraluminal pressure may be about 200 mm Hg during high amplitude pressure waves. Of course, embodiments of the pressure detection tablet allow fine detection of maximal intraluminal pressure range by giving multiple tablets, each having different preset $P_{rupture}$ values and corresponding to different colored dyes. For example, the inner coatings of the different tablets can be made of ethyl cellulose and have thicknesses which increase, as shown in FIG. 2, to provide increasing $P_{rupture}$ values, e.g., from 200 mm Hg to 225 mm Hg to 250 mm Hg. Thus, the thickness and density of the pressure-sensitive polymer are related to the rupture pressure. The relationship may be direct or linear. In alternative embodiments, a single pressure detection tablet may have multiple pressure-sensitive capsules inside the outer coating, again with different inner coating thicknesses and different colored dyes.

The inner coating may be formed from any of a variety of pressure-sensitive components. In one embodiment, the inner coating is formed from ethyl cellulose. The ethyl cellulose layer may be formed by any method known in the art. More particularly, the ethyl cellulose layer may be formed by: (1) using a gelatin capsule as a mold; (2) using a coating machine; or (3) using a dipping process.

Pressure controlled release systems for targeted drug delivery is a relatively new development and current knowledge is limited. Pressure rupture release function can be achieved by a hydrophobic layer (water insoluble) which has particular mechanical properties. Ethyl cellulose is a robust polymer that is well-adapted to providing such a hydrophobic layer. Further, ethyl cellulose provides modularity to achieve diverse functions i.e., facilitates custom design of pressure rupture parameters ($P_{rupture}$ in particular). Ethyl cellulose based coating shows positive correlation of coating thickness and capsule rupture pressure. Further, it has also been observed that lower molecular weight ethyl cellulose coatings show superior rupture properties than higher molecular weight ethyl cellulose polymers; at high molecular weight, ethyl cellulose coatings tend to become porous and may leach the inner contents (e.g., the dye) rather than rupturing. The other polymers which bear similar properties to ethyl cellulose include cellulose acetate butyrate and cellulose acetate phthalate, and any similar cellulose acetate esters. Of course the inner coating material is not particularly limiting, as long as a controlled rupture pressure may be achieved.

Dye—The indicator dye is encapsulated by the inner coating and gets released when pressure ruptures the inner coating. The indicator dye may be any one of a variety of dyes and may be made by any method known in the art. The indicator dye may be water-soluble, non-metabolizing, and biocompatible. The dye may resist degradation in the colon and be easily excreted. The indicator dye may be of a distinct color. Different colors of the indicator dye may be used for color coding different pressure detection tablets. The indicator dye may be in gel or liquid form to avoid accidental internal rupture of the inner coating before reaching distal parts of the colon. The indicator dye may be released in the descending or sigmoid colon when the pressure exceeds a given value. The released dye may then be absorbed by the colonic wall and excreted through the urine.

A list of some exemplary water-soluble, non-metabolizable, biocompatible dyes is provided in TABLE 2 below. In certain particular embodiments, the dye may be phenol red or methylene blue. Note that yellow and/or orange dyes that meet the above functionality are not considered most desirable because they tend to match the natural color of urine, and may, therefore, be difficult to detect as a visual indicator.

TABLE 2

| Color | Dyes |
| --- | --- |
| Blue | methylene blue |
| Red | phenol red, eosin, pelargonin, aurantinidine |
| Green | indigo carmine |
| Purple | cyanidin, myrtillin, tulipanin, violdelphin |
| Brown | betadine, sorbitol |
| Pink | betalain |

Methods of Making

In some embodiments, the methods of making the pressure sensitive inner coating that ruptures at or above a threshold pressure can be similar to existing methods of making pressure controlled drug capsules. Pressure controlled drug capsules make use of the intraluminal pressure that may develop in the colon for colon specific drug delivery. These capsules can withstand pressures in the small intestine and disintegrate within the lumen of the colon, due at least in part to pressure generated by high viscosity contents. Although construction of existing pressure controlled drug capsules is optimized to disintegrate at pressures significantly lower than those reported for diverticula formation, similar underlying materials and construction methods can be used for creation of encapsulation layers (both the pressure sensitive layer and the enteric coating) in the proposed pressure detection tablet.

Typical methods of preparing pressure controlled drug capsules include (1) using a gelatin capsule as a mold, (2) using a coating machine, e.g., the HICOATER-MINI coating machine, and (3) a dipping process. The last two methods have been developed for large scale manufacturing.

The first method of preparing a pressure controlled drug capsule is to use a gelatin capsule mold. An ethyl cellulose solution in methyl chloride and ethanol (1:1) is added to an empty gelatin capsule through a pore in the capsule. The inner surface of the capsule is coated by rotating it horizontally at low temperatures overnight. The gelatin capsule is dissolved in water. After drying, the drug for pressure controlled delivery may be mixed with PEG (400/1000) and filled through the pore. The drug-loaded capsule is then sealed with an ethyl cellulose glue.

The second method of preparing a pressure controlled drug capsule is to use a HI Coater-Mini coating machine to make an ethyl cellulose layer. Briefly, suppositories of PEG 1000 mixed with a drug are molded into a capsule shape. An ethanolic solution of ethyl cellulose is coated by spraying the molded capsules on a rotating pan.

A third method of making an ethyl cellulose encapsulation layer is by dipping. This method suggests double coating the capsule with ethyl cellulose as well as hydroxylpropylmethylcellulose acetate succinate ("HPMCAS"). A steel bar mold is dipped into 5% (w/v) ethanolic ethyl cellulose solution at 40° C. After drying thoroughly, it is again dipped into 8% ammonical solution of HPMCAS. The mold is rotated slowly for 3 hours at 50° C. to form a double-layered coat. The rod is removed and the mold is cut into appropriately sized capsules. A drug is mixed with PEG 1000 and is introduced into the top of the capsule. The capsule is dried and sealed with an ethanolic enteric polymer (e.g., HMPCAS).

In some embodiments, the outer coating may also be made using the dipping method (described above). The enteric coating (outer coating with pH-sensitive or bacterial degradable polymers) suggested in some embodiments of the disclosure is of Eudragit or HPMCAS. This method may be applicable to formation of both the enteric (outer coating) and colon-targeted delivery (inner coating).

Some factors that affect disintegration behavior (and dye release) of the inner coating include the type and grade of coating material used, capsule size (e.g., capsule size #0, #2, etc.; FIG. 6), thickness of coatings, and methods of manufacturing. In the literature, correlation data exists only for ethyl cellulose-based capsules where capsules of different sizes and thicknesses are studied for hardness and time of drug release.

In the literature, pressure controlled drug capsules are intended to disintegrate at luminal pressures in the colon. It is reported that the thickness of the ethyl cellulose coating determines disintegration characteristics of the capsule. The hardness of the ethyl cellulose membrane is linearly proportional to the thickness of the ethyl cellulose membrane (FIG. 6). The time delay of drug release also proportionally increases with the thickness of the ethyl cellulose membrane (FIG. 7). Colonic luminal pressure increases from the ascending to the sigmoidal colon, which causes high thickness capsules to disintegrate at delayed time. Hence, it is possible to make capsules that rupture at higher pressures by increasing the thickness of the ethyl cellulose membrane.

Applications and Methods of Using the Disclosed Pressure Detection Tablets

The disclosed pressure detection tablets can be used in many different ways. TABLE 3 provides various exemplary applications based on the particular stage of diverticula disease.

TABLE 3

| Stage of Diverticular Disease | Characteristic | Use of Pressure Detection Tablet (PDT) |
|---|---|---|
| Asymptomatic (accidental finding) | Risk of developing complications | Prevent disease development: Use PDT to regularly monitor colon pressure Take immediate prophylactic measures in case of deviances, preventing disease development |
| Symptomatic (uncomplicated/ complicated) | | Track response to therapy: Check effectiveness of treatment for pressure control (e.g., smooth muscle relaxants) Track disease progression: Create a history of colon pressure to track disease progression |
| Post-colon surgery | Critical to monitor physiological variables like pressure | Monitor at home: Monitor pressure on a daily basis to avoid risk development |

TABLE 4 provides applications for patients and physicians.

TABLE 4

| State of Health | Characteristic | Use of Pressure Detection Tablet (PDT) |
|---|---|---|
| Multiple symptoms of abdominal disorder Self-care beyond a certain age | Difficult to identify the cause of the disorder Western population above 40 years of age are prone to develop colonic disorders | Quick narrowing down: Positive test indicates that disorder is related to high colon pressures (e.g., diverticulosis or IBS) Self-monitoring: Use of PDT to weekly/bi-weekly check the colon pressures to avoid common colonic disorders (e.g., diverticulosis or IBS) Self-care: Adopt healthy habits (high fiber diet, physical exercise) and track their effectiveness |

Variant of Design

Apart from indicating the presence of abnormal intraluminal pressures, the proposed method can also be used to quantify the levels of pressure being reached inside the colon. This can be achieved through a multi-compartment design of the inner contents in which instead of a single dye, there are multiple dyes encapsulated in multiple coatings stored inside the outer coating.

As an alternate design, a multi-color pressure detection tablet can be constructed where two or more capsules of macrospheres that individually rupture at different pressure can be contained under a single outer coating as shown in FIG. 4B. For example, a tablet can be designed where three capsules of macrospheres of purple, cyan, and green can each sustain pressures of 220 mm Hg, 270 mm Hg, and 320 mm Hg, respectively, and are all encapsulated under a single outer cover (FIG. 4B).

The pressure detection tablets disclosed herein provide a basis for early stage diagnosis of predisposition of patients to otherwise asymptomatic colonic disorders as well as the basis for initiating preventing treatment(s), if necessary.

Comparative Benefits and Advantages

This disclosure provides several benefits and advantages as compared to the prior art. First, this disclosure provides a simple and inexpensive method. The method is self-administered, without requiring complicated clinical instruments or techniques to detect colonic pressures. Second, this disclosure provides for pressure detection under real conditions. Pressure build-up is detected in an unprepared colon (i.e., its real, functioning state), as compared to other methods which require a prepared colon. A prepared colon could possibly alter colonic motility and thus the pressure measurements as well. Third, the method described in this disclosure is safe. The proposed method does not expose the biological systems of the human body or the colon to any undesirable fields (as is done in certain diagnostic and imaging techniques, e.g., endoscopy), and thus is a safe method of detecting undesirable colonic changes. Fourth, the method described in this disclosure allows for response tracking. The response to effectiveness of drugs, diets, or exercise recommended for controlling colonic pressures can be readily tracked on a frequent and regular basis. Such tracking would also be useful for optimizing drug dosage (preventing over-dosage and under-dosage) and altering treatment as a disease progresses. Fifth, the method described in this disclosure provides a simple way to interpret the results. The change in urine color is easily detectable and a simple way to track pressure build-up. This method is much simpler than other methods which require specialized equipment and clinical expertise to identify a colonic disorder. Sixth, the method provided herein encourages compliance. Psychologically, it acts as a feedback directly attributable to the actions taken by the patient, helping to reinforce their compliance to the curative and/or preventative strategies suggested by the doctor. Seventh, the method provided herein may be used at home for post-operative management of gastrointestinal surgery patients. Daily pressure monitoring for patients who have undergone colon surgeries is possible at home and does not require a specific clinical environment.

EXAMPLE 1

Making a Pressure Detection Tablet with a Single Pressure Threshold Using a Gelatin Capsule as A Mold The present example outlines how to make a pressure detection tablet with a single pressure threshold using a gelatin capsule as a mold.

An indicator dye was provided in the pressure detection tablet. The indicator dye was phenol red at a concentration of 0.01% (w/v) prepared by dissolving it in water.

An inner coating was provided in the pressure detection tablet. The inner coating was prepared using a gelatin capsule as a mold. 600 mg of ethyl cellulose was added to a 16 mL solution of methyl chloride and ethanol (1:1), and the solution was stirred until the ethyl cellulose dissolved. The ethyl cellulose mixture was then poured into an empty gelatin capsule of desired size through a pore at the either the top or bottom of the capsule. The inner surface of the capsule was coated with the ethyl cellulose mixture by rotating it horizontally at a temperature of 6° C. for 12 hours. The outer gelatin capsule was dissolved in water. Upon drying, the bottom pore of the capsule was closed using ethyl cellulose glue. The indicator dye solution was poured into the capsule through the pore at the top of the capsule. The pore was sealed with an ethyl cellulose glue.

An outer coating was provided in the pressure detection tablet using a dipping method. The outer coating was prepared by dipping the capsule into an 8% ammonical solution of HPMCAS. The capsule was rotated slowly for 3 hours at 50° C. to form the outer coating.

EXAMPLE 2

Making a Pressure Detection Tablet with a Single Pressure Threshold Using a Hicoater-Mini Coating Machine The present example outlines how to make a pressure detection tablet with a single pressure threshold using a HI Coater-Mini coating machine.

An indicator dye was provided in the pressure detection tablet. The indicator dye was methylene blue at a concentration of 2.0% (w/v). The indicator dye was mixed with a suppository base, e.g., PEG1000, to form capsular-shaped suppositories. The suppositories were treated with magnesium silicate powder before being placed into the coating machine. The excess magnesium silicate was removed before the ethyl cellulose coating process.

An inner coating was provided in the pressure detection tablet. The inner coating was prepared using a HI Coater-Mini coating machine. 600 mg of ethyl cellulose was added to a 16 mL solution of methyl chloride and ethanol (1:1), and the solution was stirred until the ethyl cellulose dissolved. The ethyl cellulose mixture was then coated onto the capsules by spraying them on a rotating pan. The spraying machine had a blower temperature of 45° C. and an exhaust temperature of 25° C. The spray pressure was 2 kg/cm and the air flow-rate was 30 NI/cm. The rotating speed of the coating pan was 40 rpm. The flow rate of the ethyl cellulose coating solution was 2 mL/min for size #0 capsule. An outer coating was provided in the pressure detection tablet. The outer coating was prepared by dipping the capsule into an 8% ammonical solution of HPMCAS. The capsule was rotated slowly for 3 hours at 50° C. to form the outer coating.

EXAMPLE 3

Making a Pressure Detection Tablet with a Single Pressure Threshold Using a Dipping Method The present example outlines how to make a pressure detection tablet with a single pressure threshold using a dipping method.

An indicator dye, indigo carmine, was prepared at a concentration of 3.0% (w/v) by mixing with a suppository base, PEG400. An inner coating was provided in the pressure detection tablet. The inner coating was prepared using a dipping method. A steel bar mold was dipped into the 5% (w/v) ethanolic ethyl cellulose solution at 40° C. for 2 hours to form the inner coating.

An outer coating was provided in the pressure detection tablet. After the inner coating was thoroughly dried, the outer coating was prepared by dipping the same steel bar mold into an 8% ammonical solution of HPMCAS. The capsule was rotated slowly for 3 hours at 50° C. to form the outer coating. The bar was removed and the mold was cut into capsules of desired size. The indicator dye-mixture was poured into the capsule body and capsule cap portion. Upon hardening, the capsule body and cap were joined and sealed with an ethanolic HPMCAS solution.

EXAMPLE 4

Making a Pressure Detection Tablet With Multiple Pressure Thresholds Using a Gelatin Capsule as a Mold The present example outlines how to make a pressure detection tablet with multiple pressure thresholds using a gelatin capsule as a mold.

An indicator dye was provided in the pressure detection tablet. The indicator dye was phenol red at a concentration of 0.01% (w/v) prepared by dissolving it in water.

An inner coating was provided in the pressure detection tablet. The inner coating was prepared using a gelatin capsule as a mold. 600 mg of ethyl cellulose was added to a 16 mL solution of methyl chloride and ethanol (1:1), and the solution was stirred until the ethyl cellulose dissolved. The ethyl cellulose mixture was then poured into an empty gelatin capsule of desired size through a pore at the either the top or bottom of the capsule. The inner surface of the capsule was coated with the ethyl cellulose mixture by rotating it horizontally at a temperature of 6° C. for 12 hours. The outer gelatin capsule was dissolved in water. Upon drying, the bottom pore of the capsule was closed using ethyl cellulose glue. The indicator dye solution was poured into the capsule through the pore at the top of the capsule. The pore was sealed with an ethyl cellulose glue. Two additional ethyl cellulose capsules were similarly prepared. One was filled with methylene blue and one was filled with indigo carmine.

An outer coating was provided for each of the independent ethyl cellulose capsules using a dipping method. The outer coating was prepared by dipping the capsules into an 8% ammonical solution of HPMCAS. The capsules were rotated slowly for 3 hours at 50° C. The second and third capsules were dipped into the 8% ammonical solution of HPMCAS a second time, and again rotated slowly for 3 hours at 50° C. The third capsule was dipped into the 8% ammonical solution of HPMCAS a third time, and again rotated slowly for 3 hours at 50° C.

The three independent ethyl cellulose capsules were glued together with ethyl cellulose glue, and the pressure detection tablet was dipped into the 8% ammonical solution of HPMCAS. The pressure detection tablet was rotated slowly for 3 hours at 50° C. to form the outer coating.

EXAMPLE 5

Making a Pressure Detection Tablet with Multiple Pressure Thresholds Using a Hicoater-Mini Coating Machine The present example outlines how to make a pressure detection tablet with multiple pressure thresholds using a HI Coater-Mini coating machine.

An indicator dye was provided in the pressure detection tablet. The indicator dye was methylene blue at a concentration of 2.0% (w/v). The indicator dye was mixed with a suppository base, e.g. PEG1000, to form capsular-shaped suppositories. The suppositories were treated with magnesium silicate powder before being placed into the coating machine. The excess magnesium silicate was removed before the ethyl cellulose coating process.

An inner coating was provided in the pressure detection tablet. The inner coating was prepared using a HI Coater-Mini coating machine. 600 mg of ethyl cellulose was added to a 16 mL solution of methyl chloride and ethanol (1:1), and the solution was stirred until the ethyl cellulose dissolved. The ethyl cellulose mixture was then coated onto the capsules by spraying them on a rotating pan. The spraying machine had a blower temperature of 45° C. and an exhaust temperature of 25° C. The spray pressure was 2 kg/cm and the air flow-rate was 30 NI/cm. The rotating speed of the coating pan was 40 rpm. The flow rate of the ethyl cellulose coating solution was 2 mL/min for size #0 capsule. Two additional ethyl cellulose capsules were similarly prepared. One was filled with phenol red and one was filled with indigo carmine. An outer coating was provided for each of the independent ethyl cellulose capsules using a dipping method. The outer coating was prepared by dipping the capsules into an 8% ammonical solution of HPMCAS. The capsules were rotated slowly for 3 hours at 50° C. The second and third capsules were dipped into the 8% ammonical solution of HPMCAS a second time, and again rotated slowly for 3 hours at 50° C. The third capsule was dipped into the 8% ammonical solution of HPMCAS a third time, and again rotated slowly for 3 hours at 50° C.

The three independent ethyl cellulose capsules were glued together with ethyl cellulose glue, and the pressure detection tablet was dipped into the 8% ammonical solution of HPMCAS. The pressure detection tablet was rotated slowly for 3 hours at 50° C. to form the outer coating.

EXAMPLE 6

Making a Pressure Detection Tablet with Multiple Pressure Thresholds Using a Dipping Method The present example outlines how to make a pressure detection tablet with multiple pressure thresholds using a dipping method.

An indicator dye, indigo carmine, was prepared at a concentration of 3.0% (w/v) by dissolving it in water. An inner coating was provided in the pressure detection tablet. The inner coating was prepared using a dipping method. A steel bar mold was dipped into the 5% (w/v) ethanolic ethyl cellulose solution at 40° C. for 2 hours to form the inner coating. Two additional ethyl cellulose capsules were similarly prepared. An outer coating was provided for each of the independent ethyl cellulose capsules using a dipping method. After the inner coating of each ethyl cellulose capsules was thoroughly dried, the outer coating of each was prepared by dipping the same steel bar mold into an 8% ammonical solution of HPMCAS. Each capsule was rotated slowly for 3 hours at 50° C. to form the outer coating. The second and third capsules were dipped into the 8% ammonical solution of HPMCAS a second time, and again rotated slowly for 3 hours at 50° C. The third capsule was dipped into the 8% ammonical solution of HPMCAS a third time, and again rotated slowly for 3 hours at 50° C.

The bar was removed from each of the independent ethyl cellulose capsules and the molds were cut into capsules of a desired size.

An indicator dye was poured into each of the capsule through the pore at either the top or bottom of the capsule. The first set of capsules was filled with methylene blue, the second set of capsules was filled with phenol red, and the third set of capsules was filled with indigo carmine. Upon hardening, the capsule body and cap were joined and sealed with an ethanolic HPMCAS solution.

The independent capsules were glued together with ethyl cellulose glue in sets of three to form a pressure detection tablet, each set having one capsule with each of the respective indicator dyes. Each pressure detection tablet was dipped into the 8% ammonical solution of HPMCAS. The pressure detection tablet was rotated slowly for 3 hours at 50° C. to form the outer coating.

EXAMPLE 7

Using a Pressure Detection Tablet with a Single Pressure Threshold

The present example outlines how to use a pressure detection tablet with a single pressure threshold (as depicted in FIG. 3). First, the patient takes the pill. The pill reaches the descending colon and the outer coating dissolves. The inner coating is then exposed to intraluminal pressure.

If the intraluminal pressure is greater than the rupture pressure threshold of the inner coating, then the inner coating will rupture. The dye, being water-soluble, will be readily absorbed by the colonic wall. In this case, color will be imparted to the urine, indicating that the test is positive. When the test is positive, the doctor and/or patient can take remedial measures, such as dietary changes and use of medicines, to reduce intraluminal pressures.

If the intraluminal pressure is less than the rupture pressure of the pressure detection tablet, then the inner coating will not rupture and the pill will remain intact. In this case, the pill will be excreted through the feces and no color will be imparted to the urine, indicating that the test is negative.

EXAMPLE 8

Using a Pressure Detection Tablet with Multiple Pressure Thresholds

The present example outlines how to use a pressure detection tablet with multiple pressure thresholds (as depicted in FIGS. 4 and 5). First, the patient takes the pill. The pill reaches the descending colon and the outer coating dissolves. The three inner coatings, of varying degrees of thickness, are then exposed to intraluminal pressure.

If the intraluminal pressure is greater than the rupture pressure of any one of the inner coatings, then that inner coating will rupture, releasing its dye of a specific color which corresponds to the thickness of the inner coating. The dye, being water-soluble, will be readily absorbed by the colonic wall. In this case, the specific color will be imparted to the urine and the test will be positive. When the test is positive, the doctor and/or patient can estimate the range of pressures being reached in the colon based on the color of dye imparted to the urine. Then, the doctor and/or patient can take remedial measures, such as dietary changes and use of medicines, to reduce intraluminal pressures.

If the intraluminal pressure is less than the rupture pressure of the pressure detection tablet, then none of the inner coatings will rupture and the pill will remain intact. In this case, the pill will be excreted through the feces and no color will be imparted to the urine, indicating that the test is negative.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. For example, a health care professional may repeat the test with other embodiments of the pressure detection tablet that will provide a more accurate estimate of the pressure within a very narrow range. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein

What is claimed is:

1. A method for estimating a peak pressure within the colon of a subject, the method comprising:
providing a pressure detection tablet comprising a capsule, wherein the capsule comprises:
a water-soluble and non-metabolizable dye encapsulated within an inner coating, wherein the inner coating is configured to rupture at a pressure equal to or higher than a pressure threshold, and
an outer coating surrounding the capsule, wherein the dye is absorbed by the colon and excreted by the kidneys in urine upon rupture of the inner coating;
orally administering the pressure detection tablet to the subject;
observing a color of the subject's urine after a test period; and
estimating the peak pressure within the colon of the subject during the test period based on the color of the subject's urine.

2. The method of claim 1, wherein the outer coating is configured to provide targeted delivery of the capsule to the colon.

3. The method of claim 1, wherein a normal urine color is indicative of the peak pressure within the colon being lower than the pressure threshold and a urine color attributable to the dye is indicative of the peak pressure within the colon being equal to or higher than the pressure threshold.

4. The method of claim 1, wherein the inner coating comprises a pressure-sensitive polymer, and wherein the pressure threshold of the inner coating is selectable based on variations in at least one of a thickness, density and elasticity of the inner coating.

5. The method of claim 1, wherein the outer coating comprises a pH sensitive polymer that is insoluble at the acidic pH of the stomach and proximal small intestine and comprises a copolymer of EUDRAGIT L and EUDRAGIT S polymers and formulated to dissolve at a neutral pH, or comprises azo polymers of styrene and 2-hydroxy methyl acrylate formulated to dissolve by bacterial degradation, or comprises a combination thereof.

6. The method of claim 1, wherein the tablet comprises at least two capsules surrounded by the outer coating and wherein the at least two capsules comprise different dyes and are configured to rupture at equal to or higher than a different pressure threshold from one another.

7. The method of claim 1, wherein the dye is water-soluble and non-metabolizable.

8. The method of claim 1, wherein the outer coating comprises a pH sensitive polymer that is insoluble at the acidic pH of the stomach and proximal small intestine.

9. The method of claim 1, wherein the pressure detection tablet comprises at least two capsules surrounded by the outer coating, and wherein the at least two capsules comprise different dyes and are configured to rupture at equal to or higher than a different pressure threshold from one another.

10. The method of claim 1, further comprising administering a treatment to the subject if the peak pressure within the colon is equal to or above a pressure threshold, wherein the treatment is selected to reduce the peak pressure within the colon to below the pressure threshold.

11. The method of claim 10, wherein the treatment reduces the risk of the colonic disorder.

12. The method of claim 10, wherein the outer coating comprises a pH sensitive polymer that is insoluble at the acidic pH of the stomach and small intestine, and formulated to dissolve at a neutral pH or by bacterial degradation thereby providing a targeted delivery of the capsule to the colon.

13. The method of claim 10, wherein estimating the peak pressure within the colon of the subject during the test period based on the color of the subject's urine comprises:
    determining the peak pressure is below the pressure threshold during the test period in response to observing a normal urine color; and
    determining the peak pressure is equal to or above the pressure threshold during the test period in response to observing a urine color attributable to the dye.

14. The method of claim 10, wherein the pressure detection tablet comprises at least two capsules surrounded by the inner coating, and wherein the at least two capsules comprise different dyes and are configured to rupture at a different pressure threshold from one another.

15. The method of claim 10, wherein the method is repeated daily, biweekly, weekly, bimonthly, monthly, yearly, or as required.

16. The method of claim 10, wherein administering the treatment comprises administering a medication.

17. The method of claim 10, wherein administering the treatment comprises administering at least one of an altered diet or a physical exercise regimen.

18. The method of claim 10, wherein the inner coating comprises a pressure-sensitive ethyl cellulose polymer and the pressure threshold for rupture of the inner coating is selectable based on variations in at least one of a thickness, density and elasticity of the inner coating, and wherein the outer coating comprises a pH sensitive polymer that is formulated to be insoluble at the acidic pH of the stomach and proximal small intestine but formulated to dissolve at a neutral pH, or formulated to dissolve by bacterial degradation, or formulated to be a combination thereof.

19. The method of claim 10, wherein the pressure threshold can range from about 200 mm Hg to about 700 mm Hg.

20. The method of claim 1, wherein the outer coating comprises azo polymers of styrene and 2-hydroxy methyl acrylate, formulated to dissolve by bacterial degradation.

* * * * *